US010874527B2

(12) United States Patent
Fulton et al.

(10) Patent No.: US 10,874,527 B2
(45) Date of Patent: Dec. 29, 2020

(54) GUIDE FOR LOCATING A CUTTING BLOCK

(71) Applicant: DEPUY IRELAND UNLIMITED COMPANY, County Cork (IE)

(72) Inventors: Mark Fulton, Leeds (GB); Michael Reeve, Tadcaster (GB)

(73) Assignee: DEPUY IRELAND UNLIMITED COMPANY, Cork (IE)

( * ) Notice: Subject to any disclaimer, the term of this patent is extended or adjusted under 35 U.S.C. 154(b) by 238 days.

(21) Appl. No.: 15/746,049

(22) PCT Filed: Sep. 15, 2016

(86) PCT No.: PCT/EP2016/071872
§ 371 (c)(1),
(2) Date: Jan. 19, 2018

(87) PCT Pub. No.: WO2017/046271
PCT Pub. Date: Mar. 23, 2017

(65) Prior Publication Data
US 2018/0177610 A1    Jun. 28, 2018

(30) Foreign Application Priority Data

Sep. 17, 2015   (GB) .................................. 1516495.7

(51) Int. Cl.
*A61B 17/17*   (2006.01)
*A61B 17/15*   (2006.01)
(Continued)

(52) U.S. Cl.
CPC .......... *A61F 2/4657* (2013.01); *A61B 17/155* (2013.01); *A61B 17/1764* (2013.01);
(Continued)

(58) Field of Classification Search
CPC .. A61B 17/1764; A61B 17/155; A61F 2/4657
See application file for complete search history.

(56) References Cited

U.S. PATENT DOCUMENTS 5,423,827 A    6/1995   Mumme
5,688,281 A    11/1997  Cripe
(Continued)

FOREIGN PATENT DOCUMENTS

JP    2012040150 A    3/2012
WO    WO 14125253     8/2014

OTHER PUBLICATIONS

PCT International Search Report for International App. No. PCT/EP2016/071872 dated Nov. 16, 2016 (Nov. 16, 2016), 15 Pages.
(Continued)

*Primary Examiner* — Olivia C Chang

(57) ABSTRACT

A guide and a method for locating a cutting block on a resected distal surface of a patient's femur in a knee replacement procedure. The guide includes a first body part for positioning over the resected distal surface. The first body part includes a pair of posteriorly extending feet for engaging with the posterior condyles of the femur. The guide also includes a second body part for positioning over the resected distal surface. The second body part includes at least one pair of locator holes for locating fastener pins by which the cutting block can be fastened to the resected distal face. The first body part is removably attachable to the second body part in a plurality of discrete positions for selectively angling the second body part with respect to an anatomical feature of the patient when the feet of the first body part are engaged with the posterior condyles.

14 Claims, 11 Drawing Sheets

(51) Int. Cl.
  *A61F 2/46* (2006.01)
  *A61B 90/00* (2016.01)
(52) U.S. Cl.
  CPC ........ *A61B 90/06* (2016.02); *A61B 2090/061* (2016.02); *A61B 2090/067* (2016.02)

(56) References Cited

U.S. PATENT DOCUMENTS

| | | | |
|---|---|---|---|
| 5,776,137 A * | 7/1998 | Katz | A61B 17/155 606/102 |
| 6,193,723 B1 | 2/2001 | Cripe | |
| 6,673,077 B1 | 1/2004 | Katz | |
| 8,740,910 B2 | 6/2014 | McMillen | |
| 9,113,913 B2 | 8/2015 | Reeve | |
| 9,681,963 B2 | 6/2017 | Leslie | |
| 2004/0220583 A1 | 11/2004 | Pieczynski | |
| 2006/0052824 A1 | 3/2006 | Ransick et al. | |
| 2015/0238202 A1 | 4/2015 | Collins | |
| 2015/0209158 A1 | 7/2015 | Reeve | |
| 2016/0361178 A1 | 12/2016 | Budhabhatti et al. | |

OTHER PUBLICATIONS

GB Search Report for GB Application No. GB1516495.7 dated Feb. 26, 2016 (Feb. 26, 2016), 3 Pages.
Japanese Search Report for Corresponding Japanese Patent Application No. 2018-514313 dated Sep. 1, 2020, 9 Pages.

\* cited by examiner

GUIDE FOR LOCATING A CUTTING BLOCK

CROSS REFERENCE TO RELATED APPLICATION

This application is a National Stage 35 U.S.C. 371 of International Patent Application PCT/EP2016/071872 filed Sep. 15, 2016, claiming priority to Great Britain Patent Application 1516495.7, filed Sep. 17, 2015.

FIELD OF THE INVENTION

This invention relates to a guide for locating a cutting block on a resected distal surface of a patient's femur in a knee replacement procedure, to a surgical kit including the guide and to a method for using the guide.

BACKGROUND OF THE INVENTION

Factors on which the success of a knee replacement surgical procedure depends include selection of appropriate implant components and preparing the patient's bone so that the implants are positioned appropriately. Instruments are used widely to measure the size of the patient's bones, and to identify the proper locations on the bones where the bones should be cut to receive the implant components.

Preparing the femur to receive the chosen size of femoral component requires the surgeon to perform resection cuts on the femur. It is common for the first cut that is performed to be the distal cut. This is frequently performed before the choice of the size of the femoral component has been finalised. The positions of the anterior and posterior cuts are frequently controlled during the cutting steps using one or more cutting blocks. It is common to use one or more instruments to position a cutting block, for example relative to landmark features on the patient's bones in the vicinity of the patient's joint or other anatomical features.

A commonly employed approach to positioning a cutting block involves use of anatomical features on the femur such as Whiteside's line and the epicondylar axis.

A guide can be used to locate a cutting block on a resected distal surface of a patient's femur using fastener pins. The guide can be used to determine the appropriate placement of the fastener pins in the resected distal surface such that when the cutting block in mounted on the pins the cutting block is correctly aligned for making the desired posterior cut. The guide may itself be aligned for correct placement of the fastener pins by aligning a reference line, provided on the guide, parallel with the epicondylar axis or perpendicular to Whiteside's line WO2014/125253 describes a guide for locating a plane on which the posterior portions of the femoral condyles are to be resected in a knee replacement procedure and for locating a cutting block on a patient's femur, the guide has a posterior body part for positioning against the distal face of the femur, the posterior body part including at least one posteriorly extending tab portion for fitting against the posterior condyles, and an anterior body part having a proximal face for positioning against the distal face of the femur and an opposite face, the anterior body part being fastened to the posterior body part so that it can rotate relative to the posterior body part about an axis which is approximately perpendicular to the distal face of the femur. A lock can lock the anterior body part and the posterior body part against relative rotation. The anterior body part has a pair of locator holes formed in it for locating fastener pins by which a cutting block can be fastened to the distal face of the femur, and has a ledge extending from the opposite face to indicate the plane of the intended posterior condyle resection plane.

WO2013/068720 describes a bone sizing guide for assessing the size of an end of a bone includes a body having a foot component with a first surface to rest against an end surface of the bone and a foot extending transverse to the first surface to contact a side surface of the bone. A superstructure is coupled to the body so that the superstructure can slide relative to the body towards and away from the body, at least one of the superstructure and the body being adjustable so that the rotational direction in which the superstructure extends relative to the foot component about a first axis extending transverse to the first surface is adjustable. A stylus extends from the superstructure transverse to the first surface of the body, the stylus having a tip to contact a surface of the bone, and a scale is coupled to or formed on a first one of the superstructure and the body. An indicator is coupled to or formed on a second one of the superstructure and the body to identify a position on the scale. The identified position on the scale shifts as the superstructure slides towards or away from the body, and the identified position shifts as the superstructure rotates relative to the body without sliding motion between the superstructure and the body, such that the identified position on the scale is indicative of the distance between the stylus and the foot.

WO2014/006360 describes a measuring instrument for use during an orthopaedic surgical procedure to measure first and second distances from a reference point on a bone to first and second measurement points respectively. The measuring instrument has a first scale for displaying the first distance and a second scale for displaying the second distance. It includes a mask which can be positioned against the second scale after the first distance has been measured in a position that is selected relative to the second scale dependent on the measured first distance, to restrict the length of the second scale that is visible to the user.

SUMMARY OF THE INVENTION

Aspects of the invention are set out in the accompanying independent and dependent claims. Combinations of features from the dependent claims may be combined with features of the independent claims as appropriate and not merely as explicitly set out in the claims.

According to an aspect of the invention, there is provided a guide for locating a cutting block on a resected distal surface of a patient's femur in a knee replacement procedure, the guide comprising:

a first body part for positioning over the resected distal surface of the femur, the first body part comprising a pair of posteriorly extending feet for engaging with the posterior condyles of the femur, and a second body part for positioning over the resected distal surface of the femur, the second body part comprising at least one pair of locator holes for locating fastener pins by which the cutting block can be fastened to the resected distal face of the femur, wherein the first body part is removably attachable to the second body part in a plurality of discrete positions for angling the second body part with respect to an anatomical feature of the patient when the feet of the first body part are engaged with the posterior condyles, and wherein the guide further comprises a curved slot and an engagement member, wherein the engagement member engages with the slot for removably attaching the first body part to the second body part, and wherein the engagement member is received at a respective position along the slot in each of said plurality of discrete positions when the first body part is attached to the second body part.

According to another aspect of the invention, there is provided a method for locating a cutting block on a resected distal surface of a patient's femur in a knee replacement procedure, the method comprising:

providing a guide comprising:
a first body part having a pair of posteriorly extending feet;
a second body part comprising at least one pair of locator holes, wherein the first body part is removably attachable to the second body part in a plurality of discrete positions for angling the second body part with respect to at least one anatomical feature of the patient, and
a curved slot and an engagement member receivable at a respective position along the slot in each of said plurality of discrete positions when the first body part is attached to the second body part;
removably attaching the first body part to the second body part in one of said plurality of discrete positions, so that the engagement member engages with the slot and is received in one of said respective positions along the slot;
positioning the first body part over the resected distal surface of the femur such that the pair of posteriorly extending feet of the first body part are engaged with the posterior condyles of the femur and such that the second body part is positioned over the resected distal surface of the femur;
inserting fastener pins through the locator holes and into the resected distal surface of the femur;
removing the guide from the femur, and
mounting the cutting block on the femur using the fastener pins.

A guide according to embodiments of this invention can allow the second body part of the guide to be angled with respect to an anatomical feature of the patient during a knee replacement procedure in a manner that does not require a pivoting and/or locking mechanism to be provided between the first body part and the second body part. This can allow the complexity and manufacturing cost of the guide to be reduced.

The first body part, which can be positioned over the resected distal surface of the femur so that the posteriorly extending feet engage with the posterior condyles of the femur, can act as a base with respect to which the second body part of the guide can be angled, to angle the second body part with respect to the anatomical feature. The plurality of discreet positions may correspond to standard angles of rotation of the second body part (e.g. 0°, 3°, 5°, 7°).

In some examples, the guide may be used with either knee. For instance, the first body part may be removably attachable to the second body part in a first set of one or more positions for use with the left knee of the patient and in a second set of one or more positions for use with the right knee of the patient. In some examples, the first body part may be removably attachable to the second body part in a first plurality of positions for use with the left knee of the patient and in a second plurality of positions for use with the right knee of the patient. It is envisaged that some of the discrete positions may be suitable for use with both knees. For instance, in one of the discrete positions the first body part may be centred with respect to the second body part, corresponding to zero rotation of the second body part around the femoral axis for either knee.

In use, the surgeon may removably attach the first body part to the second body part in at least two of the plurality of discrete positions for angling the second body part with respect to at least one anatomical feature of the patient prior to inserting fastener pins upon which the cutting block can subsequently be mounted. The surgeon may, for instance, trial a number of different angles of rotation for the second body part until being satisfied that the second body part is correctly aligned with the anatomical feature. In some examples, the surgeon may switch between using different first body parts, for instance the surgeon may switch to using a first body part that can be attached in a different set of discrete positions, to allow for a different set of angles of rotation of the second body part.

Indicators may be provided on the first body part and/or the second body part to allow the surgeon to determine the discrete position in which the first body part of the guide is attached to the second body part. The indicators may indicate the angle of rotation of the second body part around the femoral anatomic axis that the discrete position corresponds to.

In one example, the first body part may include indicators for indicating an angle of rotation of the second body part for each said discrete attachment position of the first body part. The second body part may have one or more markers for reading off the angle of rotation indicated by the indicators on the first body part. These markers may also include an indication as to which knee of the patient the marker is to be used for, to read off the angle of rotation.

The slot can extend within a plane that is substantially parallel to the resected distal surface of the femur. The engagement member can include an engagement feature provided on an outer surface thereof. The engagement feature can urge against an inner surface of the slot when the first body part is attached to the second body part, so as to resist movement of the first body part relative to the second body part in a direction substantially parallel to the femoral axis.

The engagement feature on the engagement member may be an O-ring. In another example, the engagement feature may including one or more ridges for engaging with corresponding ridges or ramps located on an inner surface of the slot.

In one embodiment, the slot may be provided in the second body part and the engagement member can be provided on the first body part, although it is also envisaged that this configuration may be reversed so that the slot is be provided in the first body part and the engagement member is provided on the second body part.

The first body part or the second body part may include at least one first connection feature and the other of the first body part or the second body parts may include a plurality of second connection features, each of which can cooperate with the first connection feature to removably attach the first body part to the second body part in one the plurality of discrete positions.

For instance, the guide may include one or more pins and a plurality of corresponding holes for receiving the pin(s) when the first body part is attached to the first body part. The holes can be positioned to allow attachment of the first body part in each of said plurality of discrete positions. Once the first body part is attached to the second body part, the pins and corresponding holes can prevent movement of the first and second body parts relative to each other in a plane substantially parallel to the resected distal surface of the femur. In one embodiment, the one or more pins may be provided on the second body part and the plurality of corresponding holes can be provided on the first body part. It is also envisaged that this configuration may be reversed so that the one or more pins are provided on the first body part and the plurality of corresponding holes are provided on the second body part.

The guide may include one or more ridges and a plurality of grooves for receiving the ridges(s) when the first body part is attached to the first body part. The grooves can be positioned to allow attachment of the first body part in each of said plurality of discrete positions. Once the first body part is attached to the second body part, the ridges and corresponding grooves can prevent movement of the first and second body parts relative to each other in a plane substantially parallel to the resected distal surface of the femur. In one embodiment, the one or more ridges may be provided on the second body part and the plurality of corresponding grooves can be provided on the first body part. It is also envisaged that this configuration may be reversed so that the one or more ridges are provided on the first body part and the plurality of corresponding grooves are provided on the second body part.

A linear alignment marker may be located on the second body part for determining an angle of the second body part with respect to an anatomical feature of the patient while the feet of the first body part are engaged with the posterior condyles. During the procedure, the surgeon may select one of the discrete positions for mounting the first body part on the second body part such that the linear alignment marker is aligned parallel or perpendicular to the at least one anatomical feature of the patient. The at least one anatomical feature may, for instance, be an anatomical axis of the femur. The at least one anatomical feature may, for instance, include Whiteside's line or the epicondylar axis.

The guide can also include features for sizing the femoral component to be used. In one embodiment, the second body part includes a posterior body part to which the first body part is removably attachable, and an anterior body part. The guide can further include a stylus that is removably mounted on the anterior body part. The anterior body part of the second body part can be slidably mounted on the posterior body part of the second body part for moving a tip of the stylus to engage with the anterior cortex of the femur. A scale may be provided on the second body part for reading off the size of the femoral component according to the position of the anterior body part of the second body part relative to the posterior body part of the second body part when the tip of the stylus is engaged with the anterior cortex.

It is envisaged that the guide described herein may be a single use device. Accordingly, a method according to an embodiment of this invention may include disposing of the guide to prevent further use of the guide in any subsequent knee replacement procedure.

According to a further aspect of the invention, there is provided a surgical kit comprising a guide of the kind described above and at least one further first body part. Each first body part provided in the kit is removably attachable to the second body part in a plurality of discrete positions for angling the second body part of the guide with respect to an anatomical feature of the patient when the feet of the first body part are engaged with the posterior condyles of the femur.

According to an aspect of the invention, there is provided a guide for locating a cutting block on a resected distal surface of a patient's femur in a knee replacement procedure, the guide comprising:
 a first body part for positioning over the resected distal surface of the femur, the first body part comprising a pair of posteriorly extending feet for engaging with the posterior condyles of the femur; and a second body part for positioning over the resected distal surface of the femur, the second body part comprising at least one pair of locator holes for locating fastener pins by which the cutting block can be fastened to the resected distal face of the femur, in which one of the first and second body parts has at least one first connection feature, and the other of the first and second body parts has a plurality of second connection features, each of which can cooperate with the first connection feature to fasten the first body part to the second body part detachably in one of a plurality of discrete angular positions relative to the anatomic axis of the femur.

According to another aspect of the invention, there is provided a method for locating a cutting block on a resected distal surface of a patient's femur in a knee replacement procedure, the method comprising:
 providing a guide comprising:
  a first body part having a pair of posteriorly extending feet; and
  a second body part comprising at least one pair of locator holes, in which one of the first and second body parts has at least one first connection feature, and the other of the first and second body parts has a plurality of second connection features, each of which can cooperate with the first connection feature to fasten the first body part to the second body part detachably in one of a plurality of discrete angular positions relative to the anatomic axis of the femur;
 attaching the first body part to the second body part in one of said plurality of discrete angular positions;
 positioning the first body part over the resected distal surface of the femur such that the pair of posteriorly extending feet of the first body part are engaged with the posterior condyles of the femur and such that the second body part is positioned over the resected distal surface of the femur,
 inserting fastener pins through the locator holes and into the resected distal surface of the femur,
 removing the guide from the femur, and
 mounting the cutting block on the femur using the fastener pins.

BRIEF DESCRIPTION OF THE DRAWINGS

Embodiments of the present invention will be described hereinafter, by way of example only, with reference to the accompanying drawings in which like reference signs relate to like elements and in which.

DETAILED DESCRIPTION

Embodiments of the present invention are described in the following with reference to the accompanying drawings.

Embodiments of this invention can provide a guide for locating a cutting block on a resected distal surface of a patient's femur in a knee replacement procedure. The guide has a first body part and a second body part. The first body part can be positioned over the resected distal surface of the femur and has a pair of posteriorly extending feet for engaging with the posterior condyles of the femur in this position. The first body part is removably attachable to the second body part in a plurality of discrete positions for angling the second body part with respect to an anatomical feature of the patient, such as Whiteside's line or the epicondylar axis, when the aforementioned feet of the first body part are engaged with the posterior condyles. Thus, by removably attaching the first body part to the second body part in a selected one of the available discrete positions, the surgeon can angle the second body part with respect to the first body part appropriately such that the second body part is oriented at a desired angle with respect to the anatomical feature of the patient. Once the surgeon is satisfied that the orientation of the second body part of the guide is correct, the surgeon can insert fastener pins into the resected distal surface of the patient's femur. The second body part is provided with locator holes for locating these fastener pins. Subsequently, the guide can be removed from the femur and a cutting block can be mounted on the femur using the fastener pins. The locations of the fastener pins can determine in orientation of the cutting block, so that posterior and/or anterior cuts through the femur in the correct locations (as determined using the guide) of installing the femoral component. Accordingly, the guide can be used to place the fastener pins in the appropriate position for correct mounting of the cutting block to achieve a desired anterior and/or posterior cut through the femur during the knee replacement procedure.

Unlike prior devices, which include relatively complicated pivoting and locking mechanisms between the body parts of a guide for use in knee replacement surgery, a guide according to an embodiment of this invention has a relatively simple construction. Consequently a guide according to embodiments of this invention may be more robust and may be easier (and hence cheaper) to manufacture.

Figure 1:
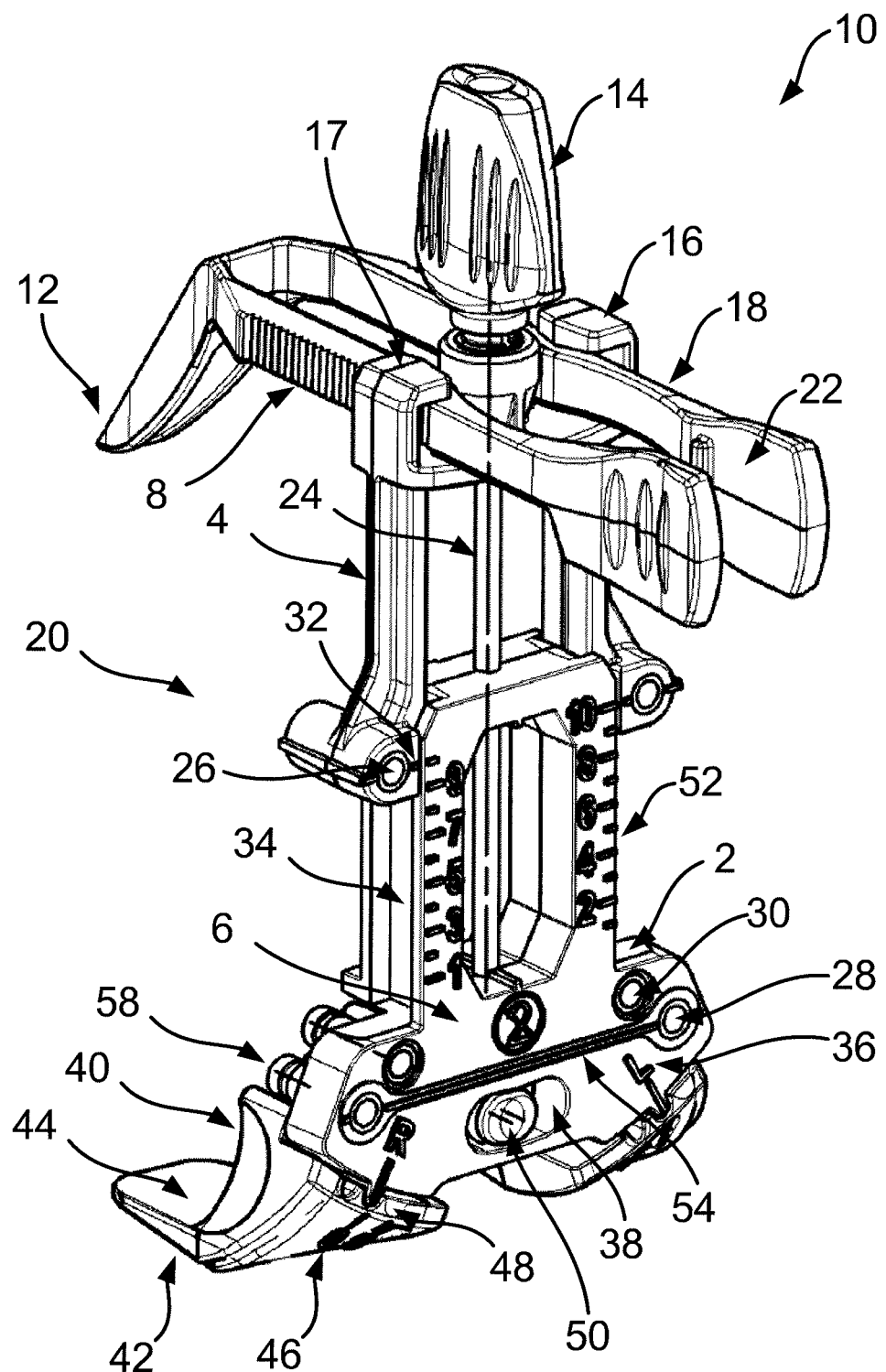
FIG. 1 shows a guide for locating a cutting block on a resected distal surface of a patient's femur in a knee replacement procedure in accordance with an embodiment of the invention.
Figure 2:
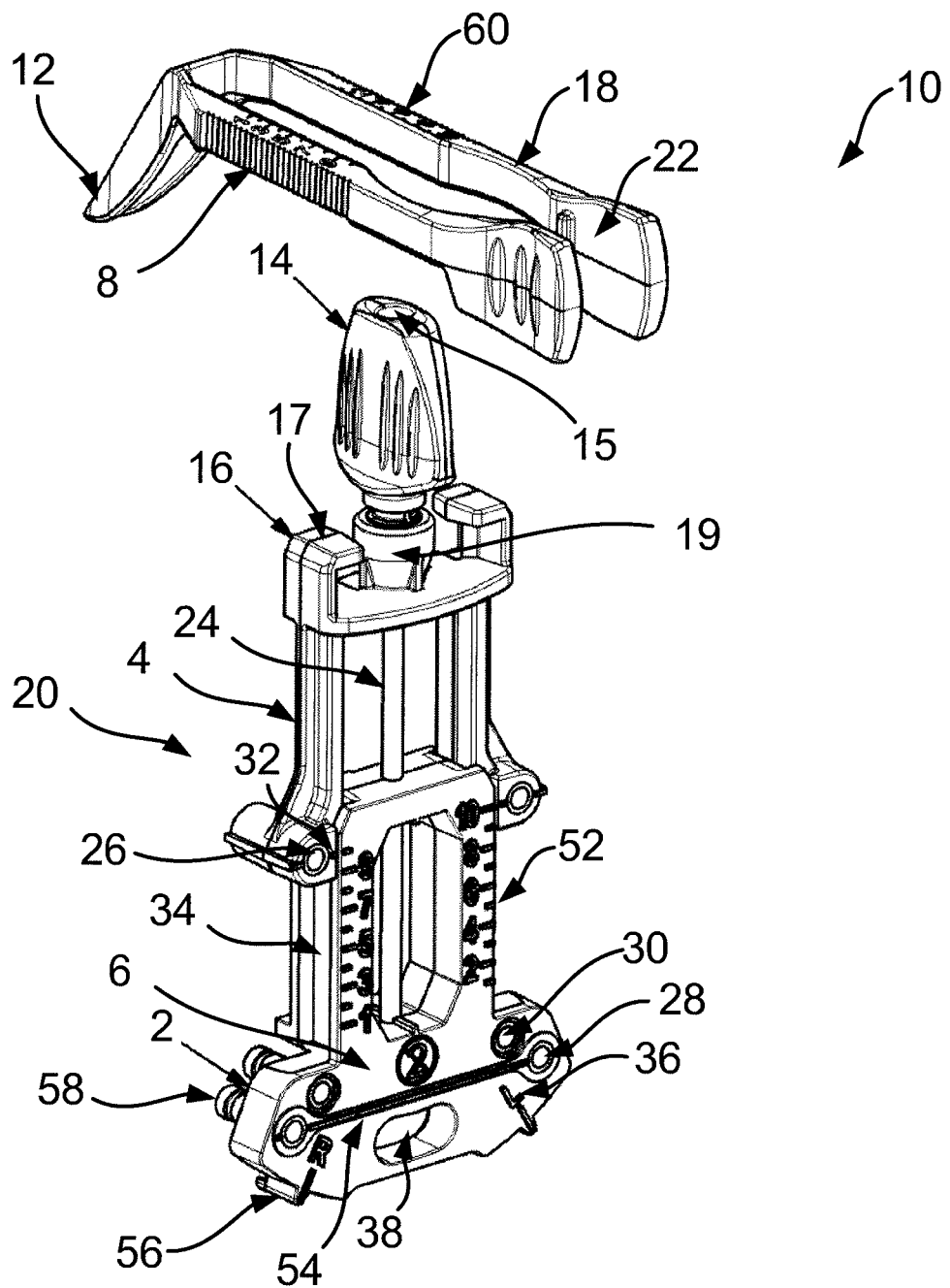
FIG. 2 shows the second body part and stylus of the guide of FIG. 1.

FIGS. 1 and 5 to 8 show a guide 10 according to an embodiment of this invention. FIG. 2 shows the second body part 20 and the stylus 8 of the guide 10, while FIGS. 3 and 4 each show an example of a first body part 40 that may be attached to the second body part 20 of the guide 10 in accordance with embodiments of this invention.

As already noted, the guide 10 includes a second body part 20 and a first body part 40. The second body part 20 has a proximal face 7 and a distal face 6. The first body part 40 has a pair of posteriorly extending feet 42. In use, the first body part 40 is placed over the resected distal surface of the femur such that a superior surface 44 of each of the pair of feet 42 engages a respective one of the posterior condyles of the femur. In this location, the second body part 20 of the guide 10 is positioned over the resected distal surface of the femur such that the proximal face 7 of the second body part 20 faces the resected distal surface and such that the distal face 6 of the second body part 20 faces away from the femur.

In order to keep the guide 10 in place while it is being used to reference from one or more anatomical features of the patient for locating fastener pins in the femur, the surgeon may press with his fingers against the distal face 6 a posterior body part 2 of the second body part 20. In some examples, to assist in holding the guider 10 in place while it is being used, one or more fixation holes 30 may be provided in the posterior body part 2 of the second body part 20. Pins such as threaded headed pins may be inserted through the fixation holes 30 and into the resected distal surface of the femur so that it is not necessary manually to hold the guide 10 against the resected distal surface. These pins may subsequently be removed when the guide itself is removed from the femur for the mounting of the cutting block.

The second body part 20 of the guide 10 also has an anterior body part 4, which is slidably attached to the posterior body part 2. The anterior body part 4 may be shaped so that it does not make contact with the resected distal surface of the femur when the first body part 40 is in position. This can allow the anterior body part 4 to slide freely with respect to the posterior body part 2 for positioning the stylus 8 as described in more detail below.

The distal face 6 of the second body part 20 includes a marker 54 which may be a linear marker such as a solid line for the surgeon to use as a reference for determining the angular alignment of the second body part 20 with respect to the anatomical feature. The linear marker 54 may, for example, comprise a groove or be painted onto the distal face 6. In some examples, the linear marker 54 may be embossed or debossed. In this example, the linear marker extends between a pair of locator holes 28. The locator holes 28, which are provided to receive fastener pins as described elsewhere herein, extend through the posterior body part 2 of the second body part 20, from the distal face 6 to the proximal face 7.

Having positioned the first body part 40 over the resected distal surface of the femur as described above, the surgeon may check the alignment of the second body part 20 against an anatomical feature such as the epicondylar axis or Whiteside's line using the linear marker 54. The sizing rod 24, which is described in more detail below, may also provide a reference for the surgeon in this respect. For instance, to judge the angular orientation of the second body part 20, the surgeon may compare the orientation of the sizing rod 24 with Whiteside's line, while comparing the orientation of the linear marker 54 to the epicondylar axis.

The first body part 40 is removably attachable to the second body part 20 in a plurality of discrete positions. Each of these discrete positions sets the second body part 20 at a respective angle to the first body part 40. Since the orientation and position of the first body part 40 is defined by the positioning of the first body part 40 over the resected distal surface such that the feet 42 engage with the posterior condyles of the femur, the angle set between the second body part 20 and the first body part 40 according to the selected discrete mounting position of the first body part determines the second body part with respect to the anatomical feature of the patient. The desired angle may, for example, be an angle which places the linear marker 54 parallel to the epicondylar axis or perpendicular to Whiteside's line. Initially, the surgeon may make an initial estimate as to the correct discrete position in which to attach the first body part 40 to the second body part 20, such that the second body part 20 is angled correctly with respect to the anatomical feature. If it is determined that at the selected discrete position of attachment of the first body part 40 to the second body part 20, the second body part 20 is not correctly angled with respect to the anatomical feature(s), the first body part 40 can be removed from the second body part 20 and attached in a different one of the discrete positions, so as to trial an alternative angle.

When the surgeon is satisfied that the second body part 20 is correctly angled with respect to the anatomical feature(s) the surgeon can locate fastener pins in the resected distal surface of the femur as noted above. The guide 10 in this example includes two pairs of locator holes through which the fastener pins may be inserted. The aforementioned pair of locator holes 28 may be used with a so called "posterior up" approach in which the fastener pins provide a fixed posterior reference for attaching a cutting block to form a fixed posterior cut. The variability in the bone cuts used in this approach (i.e. depending on the size of the femoral component to be installed) occurs at the anterior cut.

In this example, the guide 10 also includes a pair of locator holes 26 that may be used in accordance with the so called "anterior down" approach. The locator holes 26 extend through the anterior body part 4 of the second body part 20, from the distal face 6 to the proximal face 7. The superior-inferior position of the locator holes 26 can be adjusted by sliding the anterior body part 4 relative to the posterior body part 2. In the anterior down approach, fastener pins are inserted through the locator holes 26 to provide a fixed anterior reference for mounting a cutting block to make a fixed anterior cut. In this approach, the variability in the bone cuts (i.e. depending on the size of the femoral component) occurs at the posterior cut.

Note that in either case, where either the posterior up or anterior down approach is adopted, the angling of the second body part 20 with respect to the anatomical feature(s) as noted above angles the pair of locator holes 26 or 28 correctly for inserting fastener pins for mounting the cutting block at the correct angle for making the posterior and anterior cuts in the femur.

In this embodiment, the guide 10 includes a stylus 8 which may be used to size the femoral component to be used and correctly to position the locator holes 26 if the anterior down approach is used. The stylus 8 is mounted on the anterior body part 4 of the second body part 20. The anterior body part 4 is mounted on a pair of grooves 34 that are located at either side of the posterior body part 2, to allow the anterior body part 4 to slide relative to the posterior body part 2. When the guide 10 is placed over the resected distal surface of the femur, the anterior body part 4 may be slid relative to the posterior body part 2 along the grooves 34 such that a tip 12 of the stylus 8 engages with the anterior cortex of the femur. The point at which tip 12 of the stylus 8 engages with the anterior cortex may indicate the location of the anterior flange of the final implant and may also indicate the exit point of the sawblade when the anterior cut is made using the cutting block. At this position of the anterior body part 4 relative to the posterior body part 2, the scale 52 can be used to determine the size of the femoral component that will be used in the procedure. The marker 32 can be provided level with the locator holes 26 to read off the appropriate value from the scale 52. The posterior position of the tip 12 on the stylus 8 relative to the second body part 20 can affect the superior-inferior position of the anterior body part 4 relative to the posterior body part 2 at which the tip 12 engages the anterior cortex of the femur. The stylus 8 can be correctly positioned to account for this using a scale that may be provided on the stylus 8 itself. In particular, the stylus 8 may be positioned such that the appropriate size of the femoral component indicated by the scale 60 corresponds with a marking 17 provided on the shoulders 16 of the anterior body part 4 within which the stylus 8 is received (see, in particular, FIG. 5).

In this example, the stylus 8 is removably attached to the anterior body part 4 of the second body part 20. The stylus 8 may compare a pair of arms 18 that terminate distal the tip 12 in a pair of tabs 22 that may be gripped by the surgeon. The arms 18 of the stylus 8 are each received within a respective slot defined within shoulder portions 16 located at the top of the anterior body part 4 of the second body part 20. The arms 18 of the stylus 8 are biased outwardly such that they press against the slots of the shoulders 16 to hold the stylus in place. To adjust the position of the stylus 8, the surgeon may pinch the tabs 22 located at the ends of the arms 18 together to release the arms 18 from their respective slots, and then either push or pull the stylus 8 so that the correct reading of the size of the femoral component is given by the scale 60 relative to the marker 17. Once the stylus 8 has been positioned as noted above in contact with the anterior cortex of the femur, fastener pins for use in an anterior down approach of the kind previously noted may be inserted into the resected distal surface of the femur through the locator holes.

A locking knob 14 is mounted in a sleeve 19 located at the top of the anterior body part 4. The locking knob 14 has an opening 15 through which the sizing rod 24, which is fixed to the posterior body part 2, can slide as the anterior body part 4 moves relative to the posterior body part 2. The locking knob 14 can be used to lock down the position of the anterior body part 4 with respect to the posterior body part 2 while the fastener pins are being inserted into the locator holes 26. In this example, the locking knob 14 can include a split collet received within the sleeve 19. The split collet includes a thread, which is engaged with a corresponding thread located on an inner surface of the sleeve 19. To lock down the position of the anterior body part 4 with respect to the posterior body part 2, the surgeon can twist the locking knob 14. This causes the locking knob 14 to screw into the sleeve 19 whereby the split collet bears against an inner slanted surface of the sleeve 19. This in turn causes the split collet to engage with an outer surface of the sizing rod 24, fixing the anterior body part 4 in position.

Figure 3:
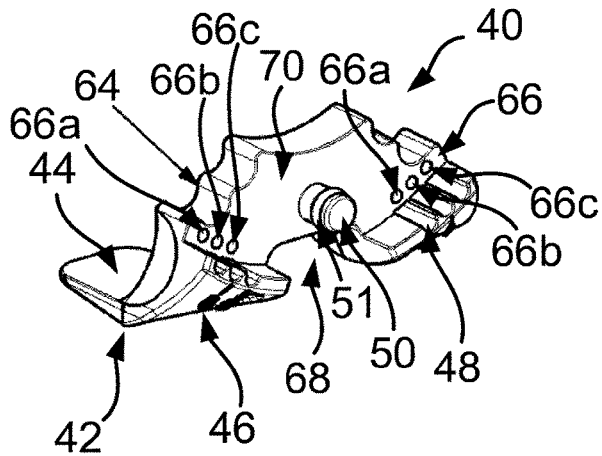
FIGS. 3 and 4 each show an example of a first body part that may be used as part of a guide in accordance with an embodiment of this invention.

FIG. 3 shows a first body part 40 of the guide 10 in accordance with an embodiment of this invention. The first body part 40 is removably attachable to the second body part 20. When the first body part 40 is attached to the second body part 20, a distal face 70 of the first body part 40 is placed against the proximal face 7 of the second body part 20.

In some examples, tubes 58 extend posteriorly from the proximal face 7 of the second body part 20 to extend the locator holes 28 and the further holes 30 toward the resected distal surface of the femur. The first body part 40 may include a number of ridges 64 to accommodate these tubes 58, so that they can pass above the first body part 40 to extend toward the femur unhindered.

The first body part 40 in this example includes an engagement member 50. The engagement member 50 extends from the distal face 70 of the first body part 40. In use, the engagement member 50 is received within a curved slot 38 of the second body part 20 when the first body part 40 is attached to the second body part 20. Engagement of the engagement member 50 with an inner surface of the slot 38 can allow the first body part 40 to be held in place once it is attached to the second body part 20. To assist in holding the first body part 40 in place, the engagement member 50 may be provided with an O-ring 51 that is mounted around an outer surface of the engagement member 50 for engagement with the aforementioned inner surface of the slot 38. It is envisaged that in some examples the locations of the slot 38 and the engagement member may be reversed so that, for instance, the engagement member extends from the proximal face 7 of the second body part 20 to be received within a slot that is located in the first body part 40.

Figure 12:
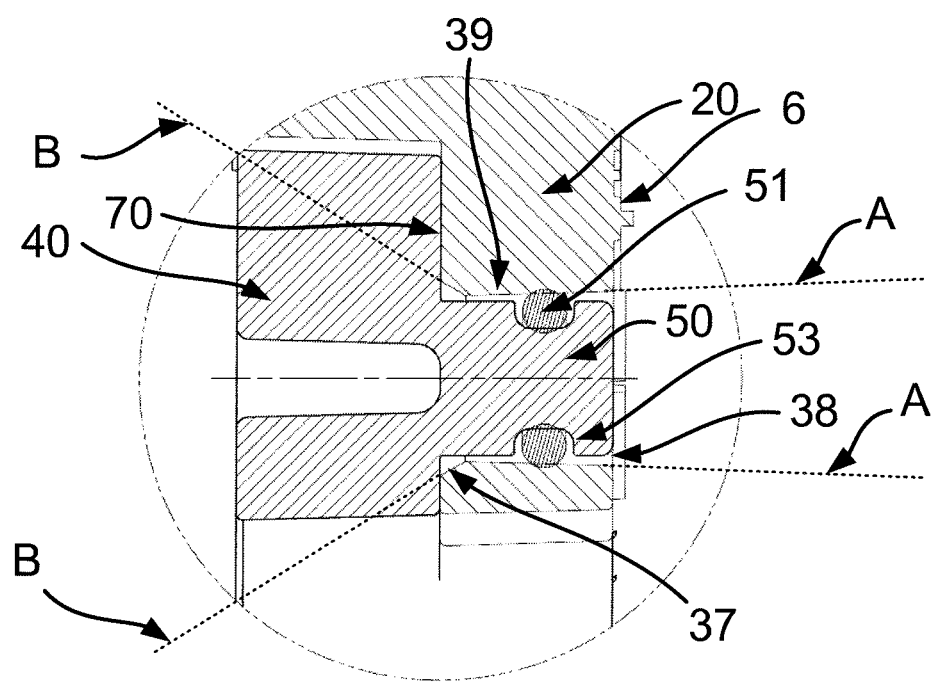
FIG. 12 shows a cross section of the slot and engagement member of the guide of FIG. 1.

FIG. 12 shows a cross section of the slot 38 and engagement member 50 of the kind described above in relation to FIGS. 1, 3 and 4. As noted above, and as can be seen in FIG. 12, in this embodiment the engagement member 50 extends from the distal face 70 of the first body part 40. The engagement member 50 in this example is substantially cylindrical, but other shapes are envisaged. The engagement member 50 is received within the slot 38 of the second body part 20.

As can be seen also in FIG. 12, in this embodiment the O-ring 51 may be located within an annular slot which runs around the outer curved surface of the engagement member 50, to urge against an inner surface of the slot 38 when the engagement member 50 is received within the slot 38.

The inner surface of the slot 38 in this embodiment includes two parts. A first tapered surface 37 extends inwardly into the slot 38 from the proximal face 7 of the second body part 20. The first tapered surface 37 is set at an angle of e.g. approximately 200 to the surface normal of the distal face 6 of the second body part 20 (the taper angle of this part is represented by the dotted line labelled B in FIG. 12). A second tapered surface 39 extends inwardly into the slot 38 from the distal face 6 of the second body part 20. The second tapered surface 39 is angled at a shallower angle (with respect to the surface normal of the distal face 6) than the first surface 37 (e.g. approximately 50). In this example, the second tapered surface 39 extends further into the slot 38 than the first tapered surface 37. The first tapered surface 37 can taper outwardly towards the proximal face 7, whereas the second tapered surface 39 can taper outwardly towards the distal face 6.

In this arrangement, the first tapered surface 37, having the steeper taper, can guide the initial insertion of the engagement member 50 into the slot 38. The interface between the first tapered surface 37 and the second tapered surface 39 (which forms a corner portion within the slot 38) can serve to initially compress the O-ring 51 as the engagement member 50 is inserted into the slot 38. The taper of the second tapered surface 39 can oppose inadvertent removal of the engagement member 50 from the slot 38, owing to the increased compression of the O-ring 50 that this would require.

It is envisaged that instead of using an O-ring 51 of the kind shown in FIG. 12, a different type of circular compressible component could be used. For instance, a snap ring (comprising a wire ring or loop, having a gap in it to allow the ring to be compressed), or a spring with an angled coil connected into a circle (for instance, of the kind known as Bal-Seal), or any other suitable form of circular compressible component could be used.

Figure 13A:
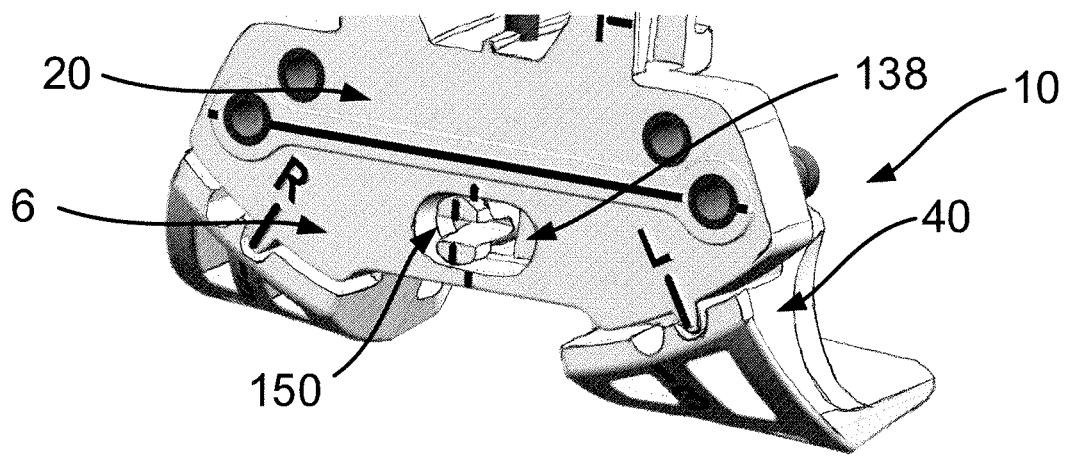
FIGS. 13A-13C show an alternative slot and engagement member for a guide of the kind shown in FIG. 1.
Figure 13B:
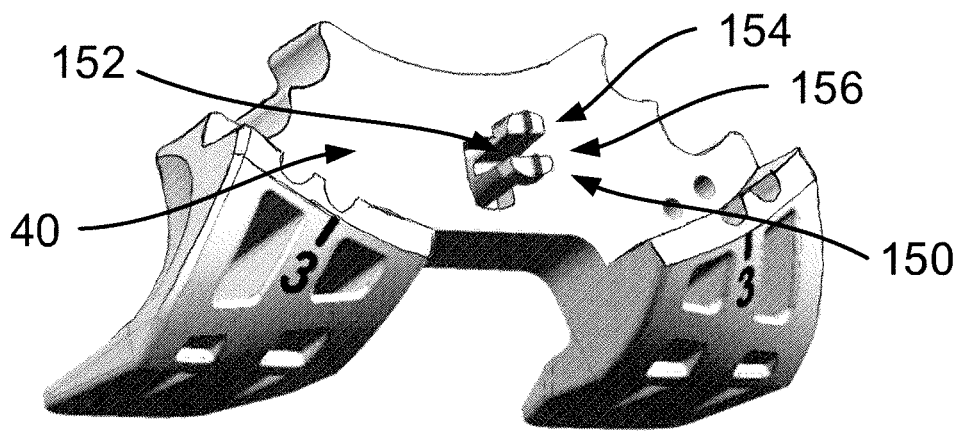
Figure 13C:
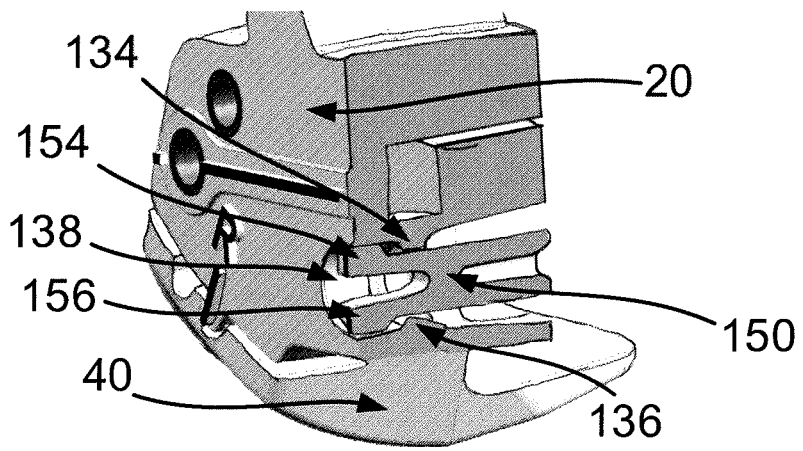

FIGS. 13A-13C show an alternative slot 138 and engagement member 150 arrangement for a guide 10 of the kind described herein. In particular, FIG. 13A shows the guide 10 with the first body part 40 attached to the second body part 20, with the engagement member 150 in position within the slot 138. As already explained previously, while in the present example the engagement member 150 extends from the distal face 70 of the first body part 40 and the slot 138 is provided in the second body part 20, it is envisaged that this arrangement may be reversed so that the slot 138 is provided in the first body part 40 and the engagement member 150 is provided in the second body part 20. FIG. 13B shows the first body part 40 in isolation, for a clearer view of the engagement member 150. A cross section of the first body part 40 and second body part 20 connected together is shown in FIG. 13C, demonstrating the way in which the features of the engagement member 150 can cooperate with the inner surface of the slot 138.

In this example the engagement member 150 includes two co-extending fingers 154, 156, which extend substantial parallel to the long axis of the engagement member 150. The fingers 154, 156 are separated by a central slot or opening 152. The fingers 154, 156 are resiliently deflectable inwards, toward the central slot or opening 152. In this configuration, the fingers 154, 156 may be compressed together as the engagement member 150 is inserted into the slot 138. This compression of the fingers 154, 156 can cause them to urge against the inner surface of the slot 138, thereby to prevent inadvertent removal of the engagement member 150 from the slot 138.

As can be seen more clearly in FIG. 13C, the fingers 154, 156 of the engagement member 150 can include outer ridges which may engage with corresponding ridges 134, 136 on the inner surface of the slot 138, to oppose removal of the engagement member 150 from the slot 138. The ridges 134, 136 reduce the inner size of the slot 138, thereby forcing the fingers 154, 156 together as the engagement member 150 is inserted into the slot 138. The presence of the ridges 134, 136 increases the amount of force required to remove the engagement member 150 from the slot 138, thereby allowing a robust attachment of the first body part 40 to the second body part 20. As can be seen in FIG. 13A, the ridges 134, 136 inside the slot 138 can run along the top and bottom of the slot 138 (within a plane parallel to the distal face 6), so as to resist removal of the engagement member 150 from the slot 138 in each of the plurality of discrete positions described herein for angling the second body part 20 with respect to an anatomical feature of the patient.

Figure 14A:
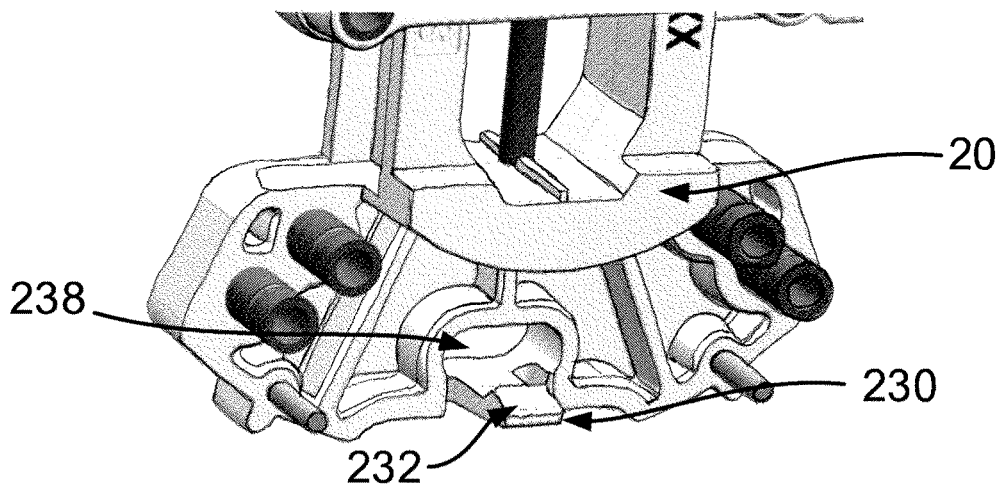
FIG. 14A-14C show another alternative slot and engagement member for a guide of the kind shown in FIG. 1.
Figure 14B:
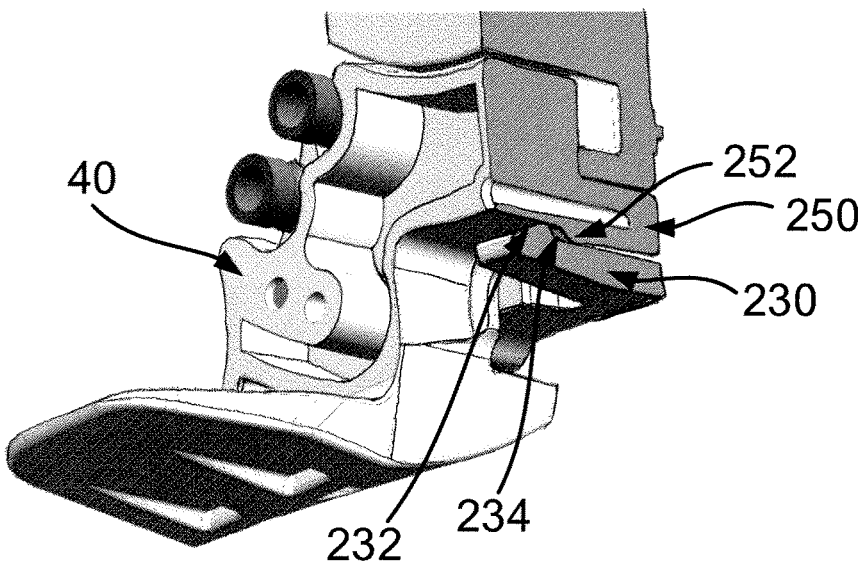
Figure 14C:
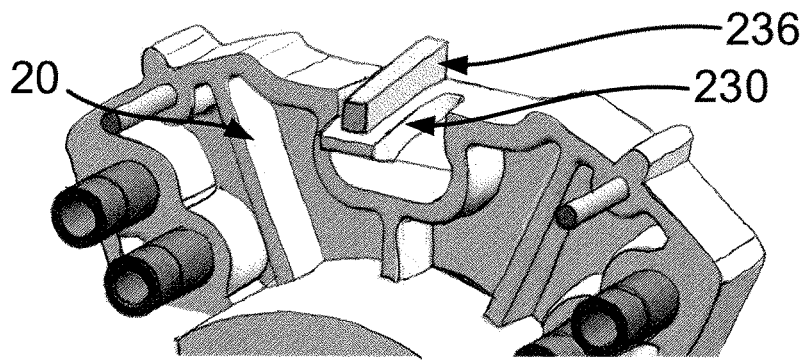

FIGS. 14A-14C show a further alternative arrangement of a slot 238 and engagement member 250 for use with the guide 10 of the kind described herein. In this example, the slot 238 is provided with a tongue portion 230 which extends proximally from the bottom of the slot 238. The tongue portion 230 is resiliently deflectable as the engagement member 250 is inserted into the slot 238. As can be seen in the cross section of FIG. 14B, the tongue 230 includes a first ramp 232 and a second ramp 234, while the engagement member 250 in this example includes a corresponding ridge 252.

In use, as the engagement member 250 is inserted into the slot 238, the first ramp 232 can guide the engagement member 250 towards the slot while the tongue 230 is deflected resiliently away from the central axis of the slot 238. As the ridge 252 of the engagement member 250 passes over the first ramp 232, the tongue 230 can deflect back towards the centre of the slot 238. When the engagement member 250 is fully received within the slot 238, the second ramp 234 which is located between the slot 238 and the first ramp 232, can act to resist removal of the engagement member 250 from the slot 238 by urging against the ramp 252.

As shown in FIG. 14C, in some examples, the tongue 230 can be provided with a strengthening member 236 and/or the thickness of the tongue 30 may be increased, thereby to increase the resilience of the tongue 230, for increasing the force required to remove the engagement member 250 from the slot 238. The strengthening member 236 may be provided on an underside of the tongue 230, opposite the slot 238 as shown in FIG. 14C.

Figure 10:
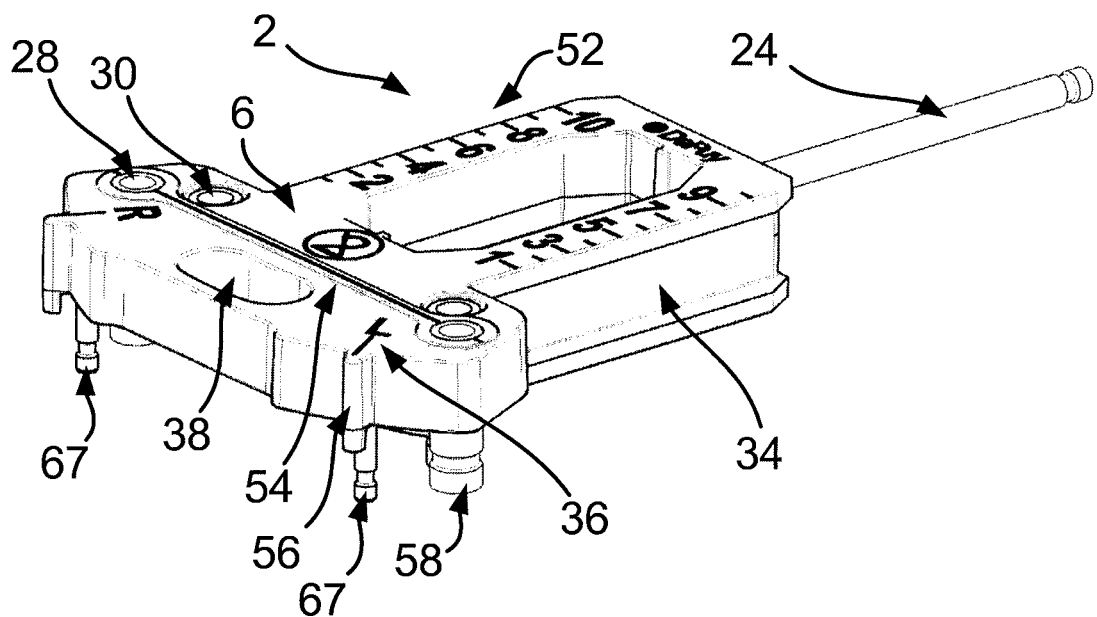
FIG. 10 shows the posterior body part of the second body part of a guide in accordance with an embodiment of this invention.
Figure 11:
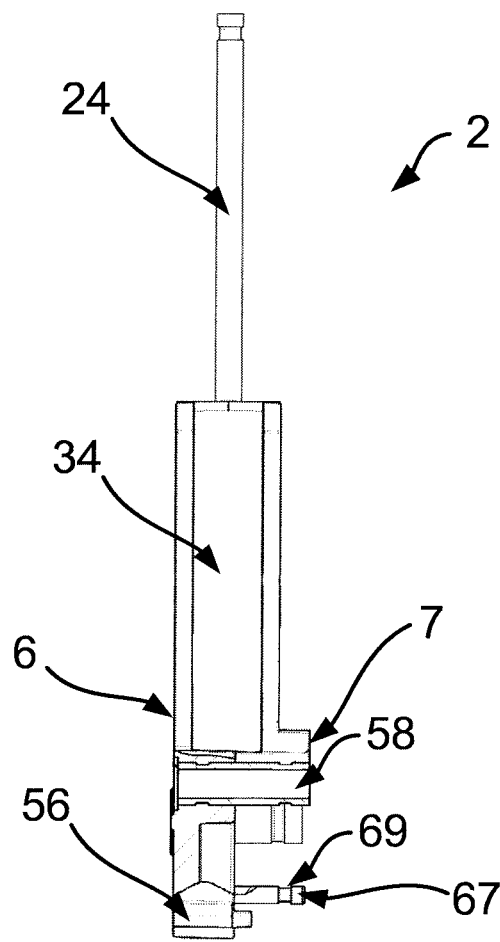
FIG. 11 shows a cross section of the posterior body part of the second body part of a guide of FIG. 10 in accordance with an embodiment of this invention.

In each of the examples described herein, the posterior body part 2 of the second body part 20 may include one or more pins 67 (e.g. visible in FIGS. 10 and 11), which extend posteriorly from the proximal face 7 of the second body part 20. These pins 67 are located to be received within corresponding holes 66 that are provided in the first body part 40. The pins 67 may include circumferential recesses 69, which may engage with corresponding ridges located within the holes 66, to provide a snap-fit attachment of the first body part 40 to the second body part 20.

The holes 66 can extend from the distal face 70 at least partially through the first body part 40. As shown in FIG. 3, the holes 66 can be provided in two rows, each row located laterally with respect to the engagement member 50. In this example, each row of holes 66 is located superiorly with respect to one of the feet 42.

To removably attach the first body part 40 to the second body part 20, the surgeon can insert the pins 67 of the second body part 20 into a pair of the holes 66, where one hole of the pair is located in one of the rows of holes 66 and the other hole of the pair is located in the other row.

Figure 9A:
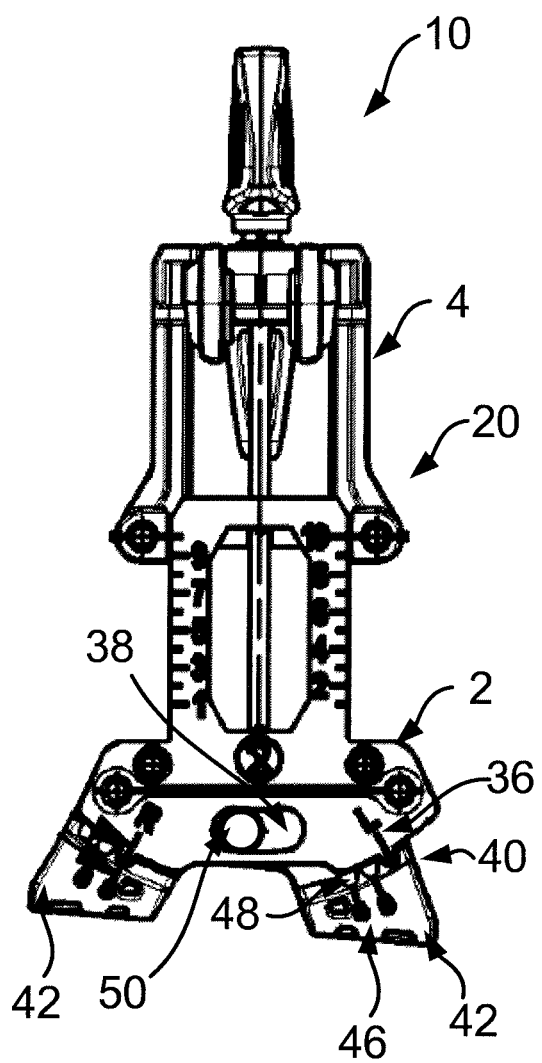
FIGS. 9A and 9B show the guide of FIG. 1 with the first body part removably attached to the second body part in a plurality of discrete positions in accordance with an embodiment of the invention.
Figure 9B:
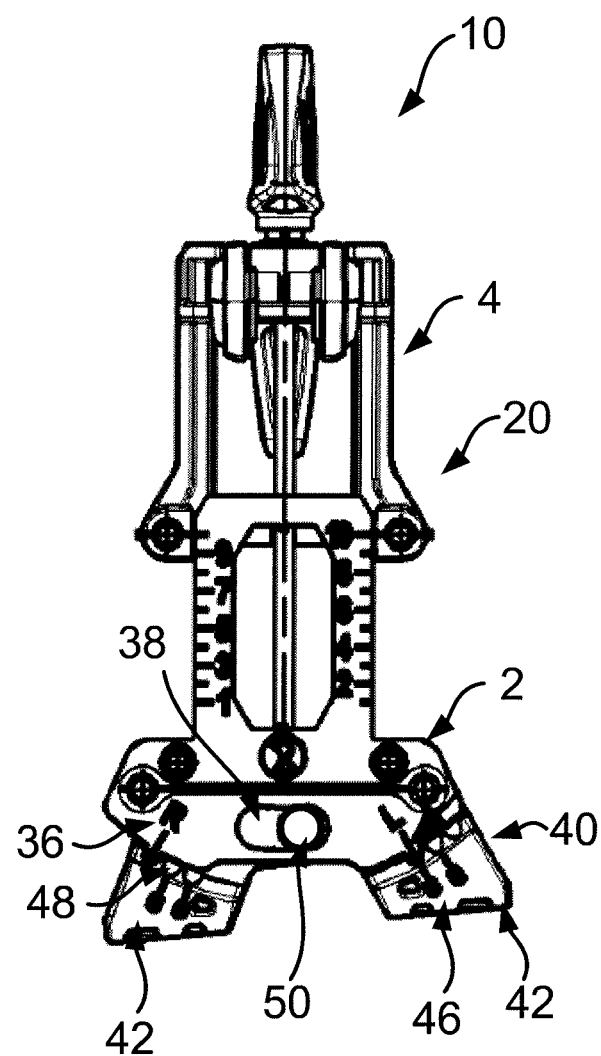

Note that the choice of holes into which the pins 67 are inserted determines an angle of rotation of the second body part 20 with respect to the first body part 40. For instance, with reference to FIG. 3, if the pins 67 are inserted into the pair of holes labelled 66b (corresponding to the configuration shown in, for example, FIG. 7) the second body part 20 is substantially centred with respect to the first body part 40. However, if the pins 67 are inserted into the pair of holes labelled 66a, then the second body part 20 is oriented at an angle to the first body part 40 as shown in FIG. 9a. Similarly, if the pins 67 are inserted into the pair of holes labelled 66c, then the second body part 20 is oriented with respect to the first body part 40 as shown in FIG. 9b. The spacing and location of the holes 66 may be selected to provide angular increments between them that correspond to standard angles of rotation of the second body part 20 to allow correct angling of the second body part 20 with respect to the above mentioned anatomical feature(s) of the patient when the first body part 40 is positioned over the resected distal surface of the femur.

Some of the holes 66 may be provided exclusively for rotation of the second body part 20 with respect to the anatomical feature(s) when operating on a right knee, whereas others of the holes may be used for angling the second body part 20 with respect to an anatomical feature(s) when operating on the left knee. However, it is also envisaged that each of the discrete positions, defined by the locations of the holes 66 and the corresponding pins 67, in which the first body part 40 may be removably attached to the second body part 20 may be suitable for use of the guide 10 with both the left knee or the right knee of the patient.

For instance, in the present example, as explained above, the holes 66b correspond to a centred position of the second body part 20 with respect to the first body part 40 and this centred position may be suitable for use when operating on either knee. However, the holes 66a in this example are used for rotating the second body part 20 only when operating on the left knee, while the holes 66c are used for providing a similar rotation (although in the opposite direction) in respect of the right knee.

In the present example, the angular increment between each pair of holes is 5°. However, it will be appreciated that this angular increment can be altered by varying the distance between adjacent holes in each row of holes 66. For instance, the angular increment between the discrete positions in which the first body part 40 can be attached to the second body part 40 may be 1°, 2°, 3°, 4°, 5°, 6° etc.).

It will also be appreciated that the direction of rotation needed for aligning the second body part 20 when operating on the right knee (anti-clockwise when viewed from behind the distal face 6 (see FIG. 9a)) is generally opposite to the direction of rotation needed for aligning the second body part 20 when operating on the left knee (clockwise when viewed from behind the distal face 6 (see FIG. 9b)).

Thus, the first body part 40 shown in FIG. 3 can allow a number of options for the rotation of the second body part 20:

Centering (zero rotation) of the second body part 20 relative to the first body part 40 using the pair of holes labelled 66b;

Anti-clockwise rotation of the second body part 20 relative to the first body part 40 using the holes 66c (when viewed facing the distal face 6 of the guide 10) for a knee replacement procedure carried out on the right knee; and Clockwise rotation of the second body part 20 by 5° relative to the first body part 40 using the holes 66a (when viewed facing the distal face 6 of the guide 10) in a knee replacement procedure carried out on the left knee.

As shown in the Figures, the first body part 40 can be provided with indicators 46 (e.g. numerical indicators) indicating the angle of rotation that is applied to the second body part 20 for each discrete position of attachment of the first body part 40 to the second body part 20. In addition to this, the second body part 20 may be provided with one or more markers 36 for reading off the angle of rotation indicated by the indicators 46. The markers 36 can be provided on the distal face 6, while the indicators 46 may be provided on a distal surface of the first body part 40, inferior the markers 36. Note that the markers 36 may further include markings such as "L" and "R" for indicating the knee (i.e. the "Left" knee or "Right" knee) of the patient that the marker 36 is to be used for, to read off the angle indicated by the indicators 46. For instance, as can be seen by comparison of FIGS. 9a and 9b, the marker 36 provided on the right hand side of the second body part 20 should be used for reading off angles relating to a knee replacement procedure on the left knee whereas the markers 36 on the left hand side should be used for reading off angles relating to a knee replacement procedure on the right knee of the patient.

As can be seen also in FIGS. 9a and 9b, the position of the engagement member 50 within the slot 38 depends upon the discrete position in which the first body part 40 is attached to the second body part 20. The elongate, curved configuration of the slot 38 can allow the engagement member 50 to be accommodated for attaching the first body part 40 to the second body part 20 in each of the different discrete positions described herein.

Returning to FIG. 3, it can be seen that the first body part 40 further includes a number of grooves 48. These grooves 48 may be located adjacent the distal face 70 of the first body part 40. In common with the holes 66, the grooves 48 may each correspond to one of the plurality of discrete positions in which the first body part 40 can be removably attached to the second body part 20. Like the holes 66, the grooves 48 may be provided in two rows, each row being located laterally with respect to the engagement member 50. The posterior body part 2 of the second body part 20 may include a pair of ridges 56, which are located to insert into a corresponding pair of the grooves 58 when the first body part 40 is attached to the second body part 20 in each of the aforementioned discrete positions. The ridges 56 (see, for example FIGS. 2 and 6) may correspond in position to the position of the markers 36 described above. The provision of the grooves 48 and the ridges 56 can provide additional structural stability for the guide 10 to prevent relative movement of the first body part 40 with respect to the second body part 20 when the first body part 40 is attached.

It is envisaged that the number of discrete positions in which the first body part 40 is removably attachable to the second body part 20 may be chosen in accordance with the requirements of the knee replacement procedure. In the example of FIG. 3, the first body part 40 is removably attachable to the second body part 20 in three discrete positions as already noted. Further (or fewer) discrete attachment positions may be provided by adding further (or providing fewer) holes 66. Also, by varying the distance between the neighbouring holes, the increments in angle for the angling of the second body part 20 between each discrete position can be determined.

Figure 4:
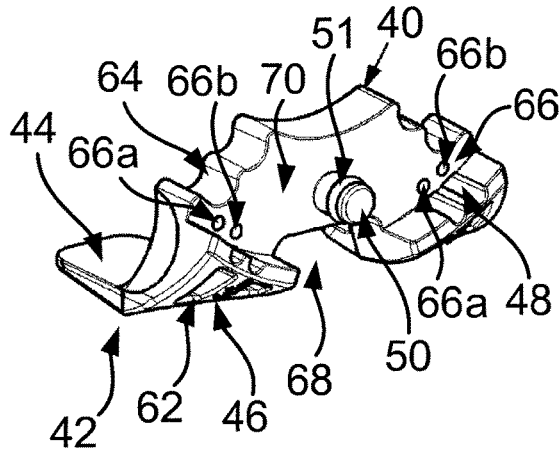
Figure 5:
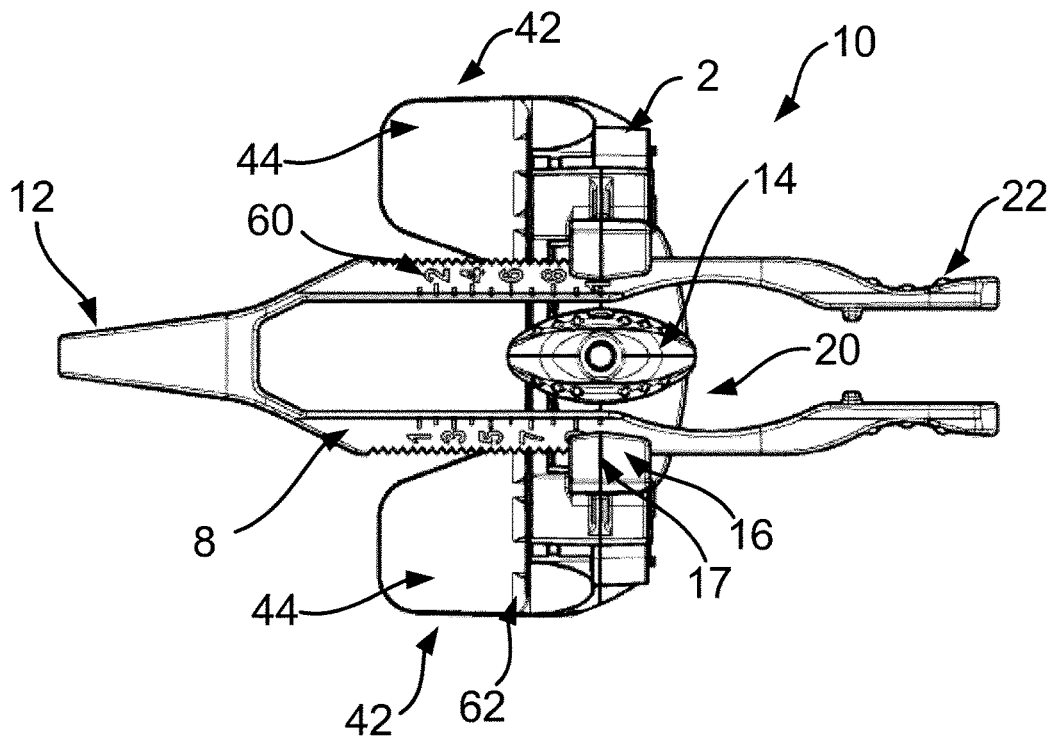
FIG. 5 shows a top view of the guide of FIG. 1.
Figure 6:
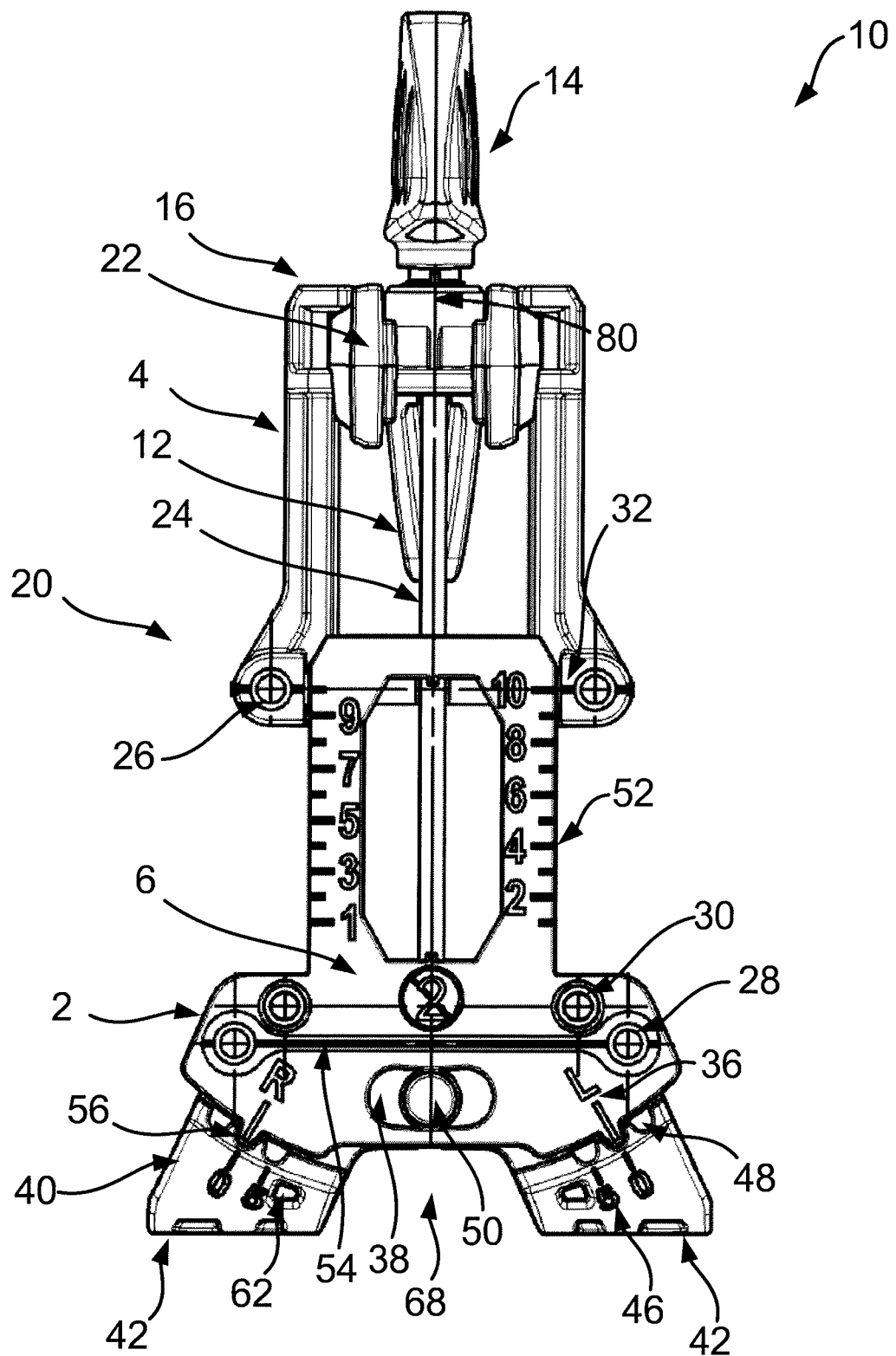
FIG. 6 shows a front view of the guide of FIG. 1.
Figure 7:
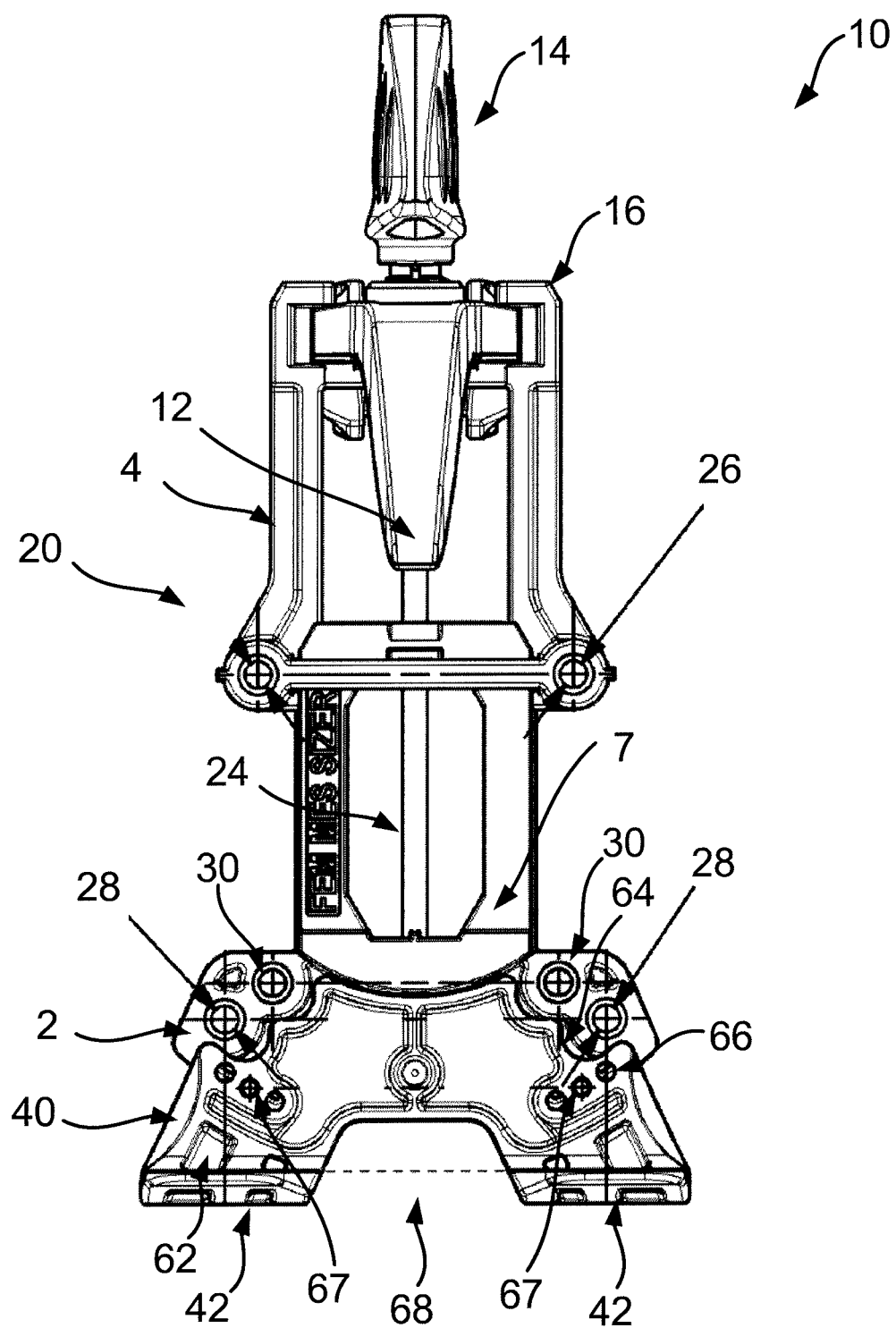
FIG. 7 shows a rear view of the guide of FIG. 1.
Figure 8:
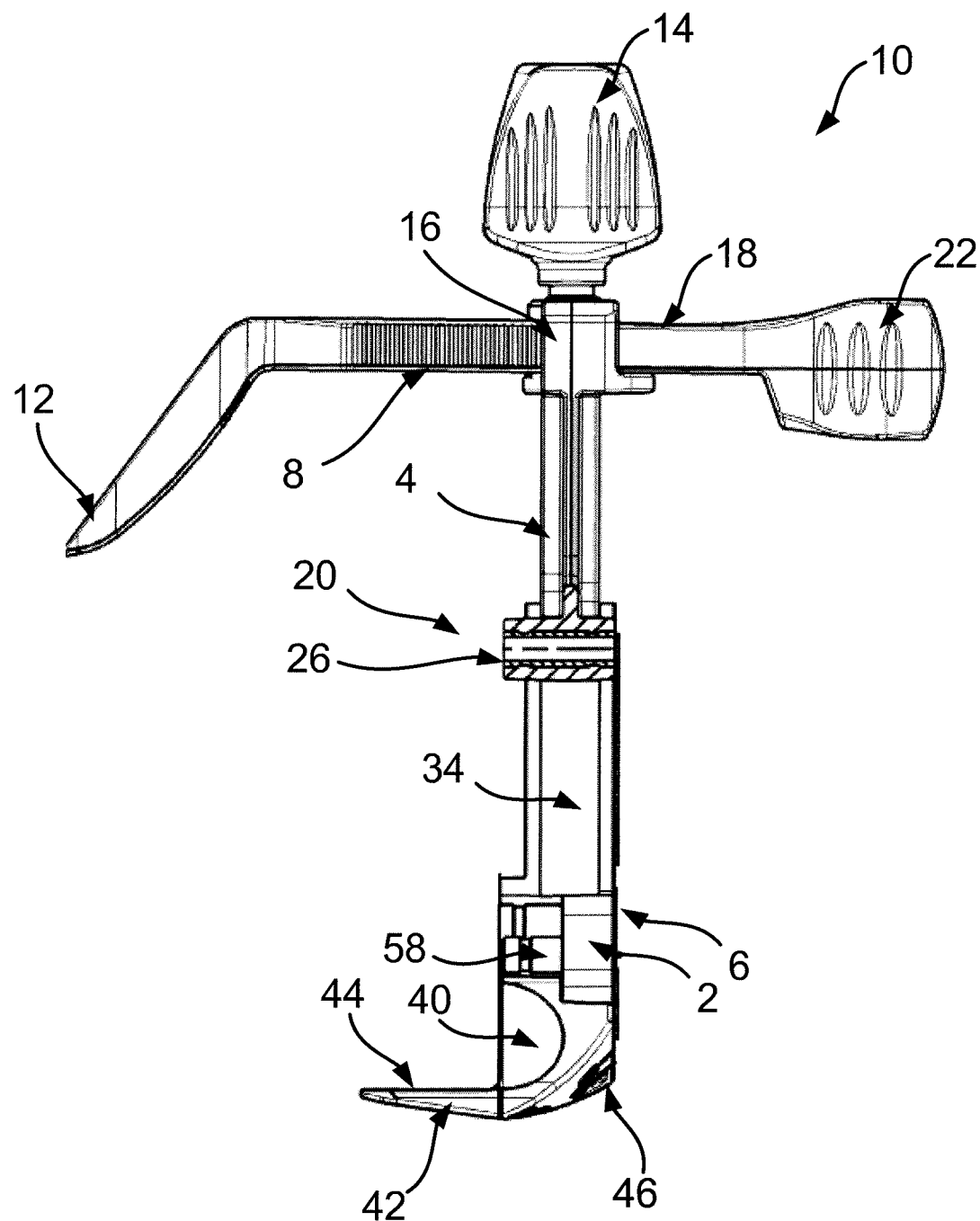
FIG. 8 shows a side view of the guide of FIG. 1.

FIG. 4 shows another example of a first body part 40 that may be used with the guide 10 in accordance with an embodiment of this invention. In the example of FIG. 4, holes 66 are provided for removably attaching the first body part 40 in only two discrete positions. In particular, the holes labelled 66a may be used for clockwise rotation of the second body part 20 by a predetermined amount (e.g. 3°) relative to the first body part 40 for use with the left knee while the holes 66b may be used for anti-clockwise rotation of the second body part 20 by the same amount (e.g. 3°) for use with the right knee.

Note that in the example of FIG. 4, none of the discrete positions is for use with both knees (e.g. there is no "centred" attachment position). Instead the first body part 40 in this example is removably attachable in two positions, one position for use with the left knee, and the other for use with the right knee, to angle the second body part 20 by the same amount in two opposite directions according to which knee is being operated on.

It is envisaged that a first body part 40 of the kind described herein may be removably attachable in more discrete positions than described in relation to FIGS. 3 and 4. For instance, if additional holes were provided in the example of FIG. 3, then more than three discrete attachment positions may be used.

The first body part 40 may include features for improving the visibility for the surgeon while using the guide 10. For instance, openings 62 may be provided through the feet 42 to allow the posterior condyles of the femur to be viewed through the feet 42 to ensure that the superior surface 44 of each foot is engaged with its respective posterior condyle. Also, a space 68 may be provided between the feet 42 to accommodate the posterior cruciate ligament and/or the tibial eminence while the guide is being used.

The guide 10 described herein may be provided as part of a surgical kit. The kit may include more than one first body parts 40. For instance, it is envisaged that the kit may include different first body parts 40 for allowing the second body part 20 to be oriented at various different angles, and with different angular increments being provided between each discrete position of attachment of the first body part 40. For instance, a surgical kit according to an embodiment of this invention may include a first body part 40 of the kind shown in FIG. 3 and also a first body part 40 of the kind shown in FIG. 4.

During a knee replacement procedure, the surgeon may switch between different first body parts in the kit in order to achieve different angular positions of the second body part 20 of the guide 10. For instance, a first body part of the kind shown in FIG. 3 may allow for angles of rotation of zero and +/−5°, while the first body part 40 shown in FIG. 4 may allow rotation of the second body part 20 at +/−30. In this way, a sufficient number of angular partitions of the second body part 20 may be enabled, to ensure that the second body part 20 can be angled correctly with respect to the at least one anatomical feature of the patient prior to insertion of the fastener pins.

Features of the guide 10 may be manufactured from engineering plastics such as polyarylamide. It is envisaged the guide 10 may be a single use device that may be discarded at the end of a knee replacement procedure to prevent subsequent use.

A knee replacement procedure may, according to embodiments of this invention, involve:
1. making a distal cut through the femur to form a resected distal face on the femur,
2. providing a guide of the kind described above;
3. removably attaching the first body part to the second body part in one of a plurality of discrete positions;
4. positioning the first body part of the guide over the resected distal surface of the femur, such that the pair of posteriorly extending feet of the first body part are engaged with the posterior condyles of the femur and such that the second body part is positioned over the resected distal surface of the femur,
5. if required, removably attaching the first body part to the second body part in another of the plurality of discrete positions (e.g. if it is judged that the orientation of the second body part is not correct) and then re-positioning the first body part of the guide over the resected distal surface of the femur,
6. if required, removably attaching a different first body part to the second body part in one of a plurality of discrete positions (e.g. if it is judged that the orientation (s) provided by the initial first body part are not suitable) and then re-positioning the guide over the resected distal surface of the femur,
7. sliding an anterior body part of the second body part relative to a posterior body part of the second body part to engage a tip of a stylus of the guide with the anterior cortex of the femur.
8. inserting fastener pins through the locator holes of the guide and into the resected distal surface of the femur;
9. removing the guide from the femur,
10. disposing of the guide to prevent further use of the guide in any subsequent knee replacement procedure;
11. mounting the cutting block on the femur using the fastener pins; and
12. using the cutting block to make an anterior or posterior cut through the femur.

Aspects of the invention are set out in the following series of numbered clauses.
1. A guide for locating a cutting block on a resected distal surface of a patient's femur in a knee replacement procedure, the guide comprising:
   a first body part for positioning over the resected distal surface of the femur, the first body part comprising a pair of posteriorly extending feet for engaging with the posterior condyles of the femur, and a second body part for positioning over the resected distal surface of the femur, the second body part comprising at least one pair of locator holes for locating fastener pins by which the cutting block can be fastened to the resected distal face of the femur, wherein the first body part is removably attachable to the second body part in a plurality of discrete positions for angling the second body part with respect to an anatomical feature of the patient when the feet of the first body part are engaged with the posterior condyles.

2. The guide of clause 1, wherein the first body part is removably attachable to the second body part in a first set of one or more positions for use with the left knee of the patient and in a second set of one or more positions for use with the right knee of the patient.

3. The guide of clause 2, wherein the first body part is removably attachable to the second body part in a first plurality of positions for use with the left knee of the patient and in a second plurality of positions for use with the right knee of the patient.

4. The guide of clause 2 or clause 3, wherein at least one of said positions is for use with both the left knee and the right knee.

5. The guide of clause 4, wherein in said position for use with both the left knee and the right knee, the first body part is centred with respect to the second body part.

6. The guide of any preceding clause, wherein the first body part comprises indicators for indicating an angle of rotation of the second body part for each said discrete attachment position of the first body part.

7. The guide of clause 6, wherein the second body part comprises one or more markers for reading off the angle of rotation indicated by the indicators on the first body part.

8. The guide of clause 7, wherein the one or more markers comprise an indication as to which knee of the patient the marker is to be used for, to read off said angle of rotation.

9. The guide of any preceding clause further comprising a curved slot and an engagement member, wherein the engagement member engages with the slot for removably attaching the first body part to the second body part, and wherein the engagement member is received at a respective position along the slot in each of said plurality of discrete positions when the first body part is attached to the first body part.

10. The guide of any preceding clause comprising one or more pins and a plurality of corresponding holes for receiving the pin(s) when the first body part is attached to the first body part, wherein the holes are positioned to allow attachment of the first body part in each of said plurality of discrete positions.

11. The guide of any preceding clause comprising one or more ridges and a plurality of corresponding grooves for receiving the ridges(s) when the first body part is attached to the first body part, wherein the grooves are positioned to allow attachment of the first body part in each of said plurality of discrete positions.

12. The guide of any preceding clause, wherein the second body part comprises a linear marking for determining an angle of the second body part with respect to an anatomical feature of the patient while the feet of the first body part are engaged with the posterior condyles.

13. The guide of any preceding clause, wherein the second body part comprises:

a posterior body part to which the first body part is removably attachable; and an anterior body part, wherein the guide further comprises a stylus removably mounted on the anterior body part of the anterior body, and wherein the anterior body part of the second body part is slidably mounted on the posterior body part of the second body part for moving a tip of the stylus to engage with the anterior cortex of the femur.

14. A surgical kit comprising a guide according to any preceding clause and at least one further said first body part, wherein each first body part is removably attachable to the second body part in a plurality of discrete positions for angling the second body part of the guide with respect to an anatomical feature of the patient when the feet of the first body part are engaged with the posterior condyles of the femur.

15. A method for locating a cutting block on a resected distal surface of a patient's femur in a knee replacement procedure, the method comprising:

providing a guide comprising:

a first body part having a pair of posteriorly extending feet; and a second body part comprising at least one pair of locator holes, wherein the first body part is removably attachable to the second body part in a plurality of discrete positions for angling the second body part with respect to at least one anatomical feature of the patient;

removably attaching the first body part to the second body part in one of said plurality of discrete positions;

positioning the first body part over the resected distal surface of the femur such that the pair of posteriorly extending feet of the first body part are engaged with the posterior condyles of the femur and such that the second body part is positioned over the resected distal surface of the femur, inserting fastener pins through the locator holes and into the resected distal surface of the femur, removing the guide from the femur, and mounting the cutting block on the femur using the fastener pins.

16. The method of clause 15 comprising removably attaching the first body part to the second body part in at least two of said plurality of discrete positions for angling the second body part with respect to at least one anatomical feature of the patient prior to inserting the fastener pins.

17. The method of clause 15 or clause 16 comprising removing the first body part from the second body part and removably attaching a different first body part to the second body part prior to inserting the fastener pins.

18. The method of any of clause 15 to 17, wherein the second body part comprises:

a posterior body part to which the first body part is removably attachable; and an anterior body part, wherein the guide further comprises a stylus removably mounted on the anterior body part, wherein the anterior body part is slidably mounted on the posterior body part of the second body part, and wherein the method further comprises sliding the anterior body part of the second body part relative to the posterior body part of the second body part to engage a tip of the stylus with the anterior cortex of the femur.

19. The method of any of clause 15 to 18, comprising aligning a linear marker located on the second body part to be parallel or perpendicular to said at least one anatomical feature of the patient.

20. The method of any of clause 15 to 19, wherein the at least one anatomical feature of the patient comprises Whiteside's line and/or the epicondylar axis.

21. The method of any of clause 15 to 20 further comprising disposing of the guide to prevent further use of the guide in any subsequent knee replacement procedure.

Accordingly, there has been described a guide and a method for locating a cutting block on a resected distal surface of a patient's femur in a knee replacement procedure. The guide includes a first body part for positioning over the resected distal surface. The first body part includes a pair of posteriorly extending feet for engaging with the posterior condyles of the femur. The guide also includes a second body part for positioning over the resected distal surface. The second body part includes at least one pair of locator holes for locating fastener pins by which the cutting block can be fastened to the resected distal face. The first body part is removably attachable to the second body part in a plurality of discrete positions for selectively angling the second body part with respect to an anatomical feature of the patient when the feet of the first body part are engaged with the posterior condyles.

Although particular embodiments of the invention have been described, it will be appreciated that many modifications/additions and/or substitutions may be made within the scope of the claimed invention.

The invention claimed is:

1. A guide for locating a cutting block on a resected distal surface of a patient's femur in a knee replacement procedure, the guide comprising:
   a first body part for positioning over the resected distal surface of the femur, the first body part comprising a pair of posteriorly extending feet for engaging with the posterior condyles of the femur; and
   a second body part for positioning over the resected distal surface of the femur, the second body part comprising at least one pair of locator holes for locating fastener pins by which the cutting block can be fastened to the resected distal face of the femur,
   wherein the first body part is removably attachable to the second body part only in a plurality of discrete positions to selectively angle the second body part with respect to an anatomical feature of the patient when the feet of the first body part are engaged with the posterior condyles, and
   wherein the guide further comprises a curved slot, a ridge, a plurality of grooves sized to receive the ridge at each position of the plurality of discrete positions, and an engagement member that extends anteriorly and is positioned between the grooves and the pair of posteriorly extending feet when viewed in a first plane, wherein each of the plurality of discrete positions is defined by one of the plurality of grooves, and the engagement member engages with the slot for removably attaching the first body part to the second body part, and wherein the engagement member is received at a respective position along the slot in each of said plurality of discrete positions when the first body part is attached to the second body part.

2. The guide of claim 1, wherein the slot extends within a plane that is substantially parallel to the resected distal surface of the femur when the second body part is positioned over said resected distal surface.

3. The guide of claim 1, wherein the engagement member includes an engagement feature provided on an outer surface thereof for urging against an inner surface of the slot when the first body part is attached to the second body part.

4. The guide of claim 1, wherein the slot is provided in the second body part and the engagement member is provided on the first body part.

5. The guide of claim 1, wherein the first body part is removably attachable to the second body part in a first set of one or more positions for use with the left knee of the patient and in a second set of one or more positions for use with the right knee of the patient.

6. The guide of claim 5, wherein the first body part is removably attachable to the second body part in a first plurality of positions for use with the left knee of the patient and in a second plurality of positions for use with the right knee of the patient.

7. The guide of claim 5, wherein at least one of said positions is for use with both the left knee and the right knee.

8. The guide of claim 7, wherein in said position for use with both the left knee and the right knee, the first body part is centered with respect to the second body part.

9. The guide of claim 1, wherein the first body part comprises indicators for indicating an angle of rotation of the second body part for each said discrete attachment position of the first body part.

10. The guide of claim 9, wherein the second body part comprises one or more markers for reading off the angle of rotation indicated by the indicators on the first body part.

11. The guide of claim 10, wherein the one or more markers comprise an indication as to which knee of the patient the marker is to be used for, to read off said angle of rotation.

12. The guide of claim 1, wherein the second body part comprises a linear marking for determining an angle of the second body part with respect to an anatomical feature of the patient while the feet of the first body part are engaged with the posterior condyles.

13. The guide of claim 1, wherein the second body part comprises:
   a posterior body part to which the first body part is removably attachable; and
   an anterior body part,
   wherein the guide further comprises a stylus removably mounted on the anterior body part of the anterior body, and
   wherein the anterior body part of the second body part is slidably mounted on the posterior body part of the second body part for moving a tip of the stylus to engage with the anterior cortex of the femur.

14. A surgical kit comprising a guide according to claim 1, wherein the first body part is one of a plurality of first body parts, each first body part being removably attachable to the second body part only in a plurality of discrete positions to selectively angle the second body part of the guide with respect to an anatomical feature of the patient when the feet of the first body part are engaged with the posterior condyles of the femur.

* * * * *